US011278468B2

(12) United States Patent
Davis et al.

(10) Patent No.: US 11,278,468 B2
(45) Date of Patent: Mar. 22, 2022

(54) THERMAL HEAT THERAPY FOAM ROLLER

(71) Applicants: Richard Davis, Owasso, OK (US); Charles Caswell, Tulsa, OK (US)

(72) Inventors: Richard Davis, Owasso, OK (US); Charles Caswell, Tulsa, OK (US)

(\*) Notice: Subject to any disclaimer, the term of this patent is extended or adjusted under 35 U.S.C. 154(b) by 178 days.

(21) Appl. No.: 15/878,402

(22) Filed: Jan. 23, 2018

(65) Prior Publication Data

US 2018/0207055 A1 Jul. 26, 2018

Related U.S. Application Data

(60) Provisional application No. 62/449,437, filed on Jan. 23, 2017.

(51) Int. Cl.
*A61H 15/02* (2006.01)
*A61F 7/00* (2006.01)
*A61H 15/00* (2006.01)

(52) U.S. Cl.
CPC ............ *A61H 15/02* (2013.01); *A61F 7/007* (2013.01); *A61F 2007/0078* (2013.01); *A61H 2015/0014* (2013.01); *A61H 2201/0207* (2013.01); *A61H 2201/0228* (2013.01)

(58) Field of Classification Search
CPC .... A61H 2015/0014; A61H 2015/0021; A61H 15/02; A61H 15/0092; D21F 3/08; B05C 1/08; B29D 99/0035; B29L 2031/324; B29L 2031/326; B41F 31/26; B41L 23/18; B41L 27/28; B21D 19/04; B26F 1/42; B22F 3/18; B21B 2203/18; B21B 2203/185; B21B 2203/187; B21B 27/00; B21B 27/005; B21B 27/02; B21B 27/06
USPC .................. 601/19, 20, 52, 63, 94, 99, 102; D24/211; 132/55; 492/1, 5, 6, 7, 14, 15, 492/16, 18, 20, 21, 22, 23, 24, 25, 26, 32, 492/33, 36, 46, 57, 60
See application file for complete search history.

(56) References Cited

U.S. PATENT DOCUMENTS

| 8,556,837 B1* | 10/2013 | Poirier ................... A61H 15/00 601/46 |
| 2004/0137326 A1* | 7/2004 | Munshi ................... H01M 4/00 429/231.4 |
| 2013/0231594 A1* | 9/2013 | Bennett .............. A61H 15/0092 601/19 |
| 2016/0238065 A1* | 8/2016 | Otten ....................... B41F 13/10 |
| 2016/0279018 A1* | 9/2016 | Egan ....................... A61H 15/02 |
| 2017/0020774 A1* | 1/2017 | Rocklin .................. A61F 7/007 |
| 2018/0049941 A1* | 2/2018 | Venezia ................. A61H 15/02 |

\* cited by examiner

*Primary Examiner* — Margaret M Luarca
*Assistant Examiner* — Cana A Gallegos
(74) *Attorney, Agent, or Firm* — Aj D. Martinez; Sherwood, McCormick & Robert

(57) ABSTRACT

A thermal heat therapy massage roller which includes a cylindrical roller core with interior structural supports, a heating element, a pliable thermally-conductive foam roller body, which is battery operated and due to its thermal capabilities is effective in relieving painful muscle or connective tissue conditions and provides a comfortable thermal option as an exercise, stretching, and core strengthening apparatus.

16 Claims, 1 Drawing Sheet

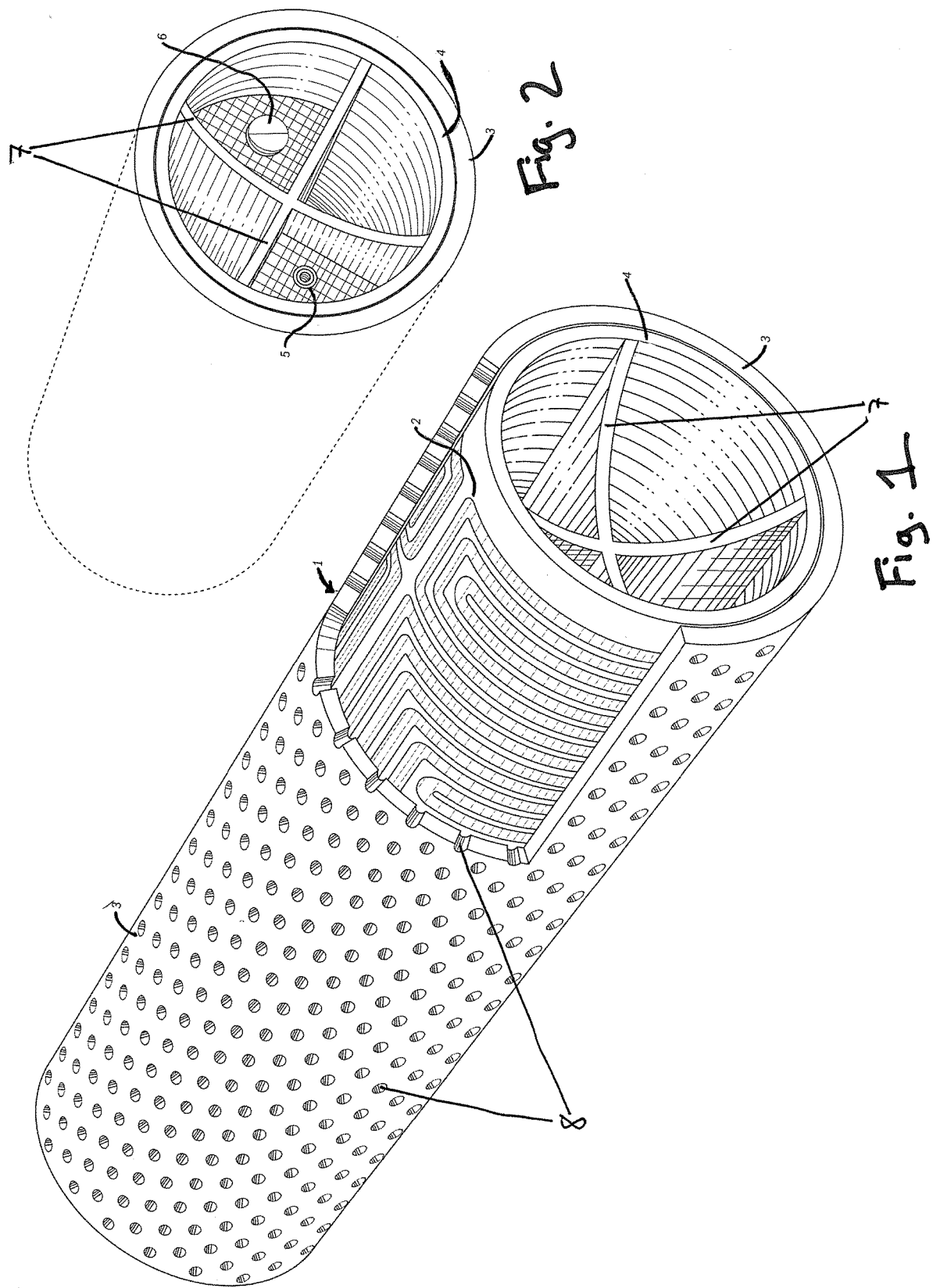

THERMAL HEAT THERAPY FOAM ROLLER

CROSS-REFERENCE TO RELATED APPLICATIONS

This Application claims the priority of U.S. Provisional Application No. 62/449,437 filed on Jan. 23, 2017.

STATEMENT REGARDING FEDERALLY SPONSORED RESEARCH OR DEVELOPMENT

Not applicable.

BACKGROUND

The present invention relates to massage, rollers, specifically massage rollers with a thermal capability. More particularly, the present disclosure is directed to a foam massage roller which has a battery-operated heating element integrated within and perforated heat exchanging foam body which is effective in relieving painful muscle or connective tissue conditions and provides a comfortable thermal option as an exercise, stretching, and core strengthening apparatus.

Massage rollers are used for a variety of reasons, including in physical therapy and exercise, and are sold in a variety of lengths, diameters, densities, and colors. Massage rollers are often used to alleviate muscle tightness and tension, as well as a core workout and strengthening apparatus. However, massage rollers may be therapeutically limited without thermal capability.

Heat has long been used in combination with massage and other physical therapy and exercise routines to confer physiological benefits and increase a user's comfort, such as when using a massage roller. Conventionally, to achieve the heating effect while using a massage roller would require a person to try a variety of impractical, inferior or dangerous options, from wrapping the roller with a heating pad, to preheating the targeted area of the body before using the roller, to using the foam roller in a heated environment, to filling a roller with heated liquid, to microwaving the roller. All of these options are inefficient, dangerous, uncomfortable or simply do not work.

Accordingly, a new and improved massage roller is needed which incorporates a thermal capability into the massage roller in an efficient, yet safe and effective manner and which is particularly effective in massaging and relieving pain and discomfort associated with muscle and connective tissue tightness and tension as well as providing a comfortable thermal option as an exercise, stretching, and core strengthening apparatus.

SUMMARY

The present invention is directed to a foam massage roller which incorporates a heating element in an efficient, safe and effective manner which is particularly effective in providing the benefits of heat with the massage roller in order to relieve pain and discomfort associated with muscle and connective tissue tightness and tension as well as providing a comfortable thermal option as an exercise, stretching and core strengthening apparatus.

An illustrative embodiment of the thermal massage roller includes a cylindrical roller core with interior structural supports that extend radially a full radial width from a shared intersection located at a center point of the roller core as further shown in the figures and described herein and which may be referred to as fins or an x-core design running the length of the core, a battery-powered heating element on the exterior of the roller core which is preferably rechargeable but may be powered by replaceable batteries, and a perforated or otherwise thermally-permeable massage roller foam body. In this illustrative embodiment, the roller core is designed to contain the rechargeable battery/power source for the heating element and a power switch for which to turn on the heating element.

While it is to be understood that both the foregoing general description and the following detailed description are exemplary and explanatory only and are not restrictive on the present invention, these and other features, aspects, and advantages of the present invention will become better understood with regard to the following detailed description and accompanying drawings where:

BRIEF DESCRIPTION OF THE DRAWINGS

FIG. 1 is a perspective view of a massage roller showing the finned roller core, heating element on the core, and the foam massage roller body of the disclosed embodiment of the present invention;

FIG. 2 is a perspective view of the massage roller showing the location of the rechargeable input and power switch contained within the finned roller core of the disclosed embodiment of the present invention;

DESCRIPTION

Referring now to the drawings, with reference to FIG. 1, there is shown a perspective view of an illustrative embodiment of a thermal massage roller 1. The thermal massage roller may include a roller core 4, a heating element 2, and a massage roller body 3.

FIG. 2 is a perspective view of the illustrative embodiment focusing on one end of the thermal massage roller shown in FIG. 1. As shown therein, the thermal massage roller may include a rechargeable power source input 5 connected to a rechargeable power source (not shown as it is located in the interior of the roller core) and power switch 6 enclosed within the roller core 4. Further, the power source may be comprised of replaceable batteries, such as AA batteries, as the power source rather than a rechargeable battery source.

The roller core 4 may have a cylindrical shape and may be made from a molded hard plastic, such as PVC (polyvinylchloride), PPE (polyphenylene), or other suitable rigid material. The roller core 4 may include a plurality of interior structural supports 7 which extend throughout the roller core interior from end to end and which extend radially a full radial width from, a shared intersection located at a center point of the roller core 4. In the present embodiment, four interior structural supports 7 are used which separate the interior of the roller core 4 into quadrants. The roller core 4 in the present embodiment is sometimes referred to as a finned roller core or X-core.

In the preferred embodiment, the ends of the interior structural supports 7 are concave as depicted in the figures, but may fully extend to the ends of the roller core 4.

In the preferred embodiment as depicted in FIG. 1. The heating element 2 may be provided on the exterior surface of the roller core 4 and may be made from an electro-thermal film or other suitable heating element. In another embodiment of the present invention, the heating element 2 may be integrated within the massage roller body 3.

In the preferred embodiment, the massage roller body 3 may be provided on the outside of the roller core 4 and heating element 2. The massage roller body 3 may contain a plurality of perforations 8 which may extend the full thickness of the massage roller body 3 and which allow the heat produced by the heating element 2 to transfer or permeate throughout the roller body 3 to the surface of the thermal massage roller 1 that comes into contact with a user's body. The massage roller body 3 may be made of closed cell foam or other resilient or pliant material that is not too hard or not too soft and is thermally-conductive or permeable.

The rechargeable power source may be a lithium ion battery or other rechargeable battery type or the power source may consist of replaceable batteries. The rechargeable power source may be enclosed within an interior cavity or quadrant of the roller core 4. The power switch 6 which controls the rechargeable power source 9 may also be enclosed at an end of an interior cavity or quadrant of the roller core 4.

While the above description of the preferred embodiment is deemed sufficient to permit those skilled in the art to practice the concepts of the present invention, it is to be appreciated that the invention may be embodied otherwise than is herein specifically shown and described and that, within said embodiment, certain changes may be made in the form and arrangement of the parts without departing from the underlying ideas or principles. Further, it is within the ambit of the present invention to cover any obvious modifications of the preferred embodiment described herein.

What is claimed is:

1. A thermal heat therapy foam roller comprising:
   a one-piece cylindrical roller core having:
      a first end and a second end;
      an exterior surface;
      a plurality of interior structural supports running longitudinally from the first end to the second end, creating a plurality of interior cavities;
      wherein said plurality of interior structural supports each extend radially a full radial width from a shared intersection located at a center point of the roller core thereby forming an X-core;
   a roller body provided on the exterior surface of the roller core;
   a heating element;
   a power source for providing power to the heating element.

2. The roller of claim 1, wherein the roller body is made of a pliable, thermally-conductive or permeable material such that heat from the heating element is transferred to the surface of the roller body.

3. The roller of claim 2, wherein the material of the roller body includes closed-cell foam.

4. The roller of claim 1, wherein the roller body further comprises a plurality of perforations to aid in the heat from the heating element being transferred to the surface of the roller body.

5. The roller of claim 1, wherein the heating element is provided on the exterior surface of the roller core between the roller body and the exterior surface of the roller core.

6. The roller of claim 1, wherein the heating element is integrated within the roller body.

7. The roller of claim 1, wherein the heating element is made from an electro-thermal film material.

8. The roller of claim 1, wherein the plurality of interior structural supports have a concave shape at each of the first and second ends.

9. The roller of claim 1, wherein the number of interior structural supports is four, separating the interior of the roller core into quadrants.

10. The roller of claim 1, wherein the power source is located within one of the interior cavities.

11. The roller of claim 1, wherein the power source comprises replaceable batteries.

12. The roller of claim 1, wherein the power source comprises a rechargeable battery.

13. The roller of claim 12, wherein the rechargeable battery is a lithium-ion type battery.

14. The roller of claim 12, further comprising a charging port input for charging said rechargeable battery.

15. The roller of claim 14, wherein the charging port input is located at the end of one of the interior cavities.

16. The roller of claim 1, further comprising a power switch located at the end of one of the interior cavities.

* * * * *